United States Patent [19]

Lee et al.

[11] Patent Number: 5,672,475

[45] Date of Patent: Sep. 30, 1997

[54] MIXED LUMINESCENT CONJUGATE TEST

[75] Inventors: Michael J. Lee, Sherborn, Mass.; Howard H. Weetall, Rockville, Md.; Joseph E. Connolly, Dedham, Mass.

[73] Assignee: Chiron Diagnostics Corporation, E. Walpole, Mass.

[21] Appl. No.: 375,466

[22] Filed: Jan. 20, 1995

Related U.S. Application Data

[63] Continuation of Ser. No. 58,617, May 6, 1993, abandoned.

[51] Int. Cl.$^6$ .............................. C12Q 1/68; G01N 33/53
[52] U.S. Cl. ................... 435/6; 435/7.72; 435/28; 435/968; 435/973; 436/518; 436/523; 436/172
[58] Field of Search ....................... 435/6, 7.72, 7.7, 435/28, 967, 968, 973, 975; 436/518, 523, 526, 528, 172, 805

[56] References Cited

U.S. PATENT DOCUMENTS

| | | | |
|---|---|---|---|
| 3,654,090 | 4/1972 | Schuurs et al. | 435/7.93 |
| 3,689,351 | 9/1972 | Ullman | 156/552 |
| 3,791,932 | 2/1974 | Schuurs et al. | 435/7.8 |
| 3,867,517 | 2/1975 | Ling | 436/531 |
| 3,996,345 | 12/1976 | Ullman et al. | 436/537 |
| 4,016,043 | 4/1977 | Schuurs et al. | 435/5 |
| 4,098,876 | 7/1978 | Piasio et al. | 436/500 |
| 4,174,384 | 11/1979 | Ullman et al. | 436/537 |
| 4,220,450 | 9/1980 | Maggio | 436/537 |
| 4,233,402 | 11/1980 | Maggio et al. | 435/5 |
| 4,261,968 | 4/1981 | Ullman et al. | 436/546 |
| 4,297,273 | 10/1981 | Buckler et al. | 530/391.5 |
| 4,302,534 | 11/1981 | Halmann et al. | 435/5 |
| 4,308,026 | 12/1981 | Mochida et al. | 436/520 |
| 4,374,120 | 2/1983 | Soini et al. | 436/546 |
| 4,385,126 | 5/1983 | Chen et al. | 436/518 |
| 4,491,634 | 1/1985 | Frenzel | 436/518 |
| 4,587,223 | 5/1986 | Soini et al. | 436/536 |
| 4,598,044 | 7/1986 | Kricka et al. | 435/7.9 |
| 4,931,223 | 6/1990 | Bronstein et al. | 252/700 |
| 5,089,630 | 2/1992 | Bronstein et al. | 549/220 |
| 5,206,179 | 4/1993 | Ramsey | 436/537 |

FOREIGN PATENT DOCUMENTS

| | | | |
|---|---|---|---|
| 0070687 | 1/1983 | European Pat. Off. | |
| 0421788A3 | 4/1990 | European Pat. Off. | C12Q 1/28 |
| 2026159 | 7/1979 | United Kingdom | G01N 33/533 |
| 2233450 | 1/1991 | United Kingdom | |
| WO90/00168 | 1/1990 | WIPO | C07D 305/04 |
| WO91/00511 | 1/1991 | WIPO | G01N 21/76 |
| WO92/12255 | 7/1992 | WIPO | C12Q 1/00 |

OTHER PUBLICATIONS

Schmidt, B.L., "A Rapid Chemiluminescence Detection Method . . . ", *J. of Virological Methods*, vol. 32, pp. 233–244 (1991).

Lenton, E.A., et al., "An Assessment of the Dual–Enzyme Immunoassay . . . ", *Human Reproduction*, vol. 4, No. 4, pp. 378–380 (1989).

Barnard, G., et al., "The Development of Non–Separation . . . ", *J. of Bioluminescence and Chemiluminescence*, vol. 4, pp. 177–184 (1989).

Anthony, F., et al., "The OVELIA Assay . . . ", *Human Reproduction*, vol. 3, No. 7, pp. 870–872 (1988).

Thorpe, G.H.G., et al. "Phenols as Enhancers . . . ", *Clin. Chem.*, vol. 31, No. 8, pp. 1335–1341 (1985).

Ekins, R., et al., "Fluorescence Spectroscopy . . . " *Clinica Chimica Acta*, vol. 194, pp. 91–114 (1990).

Shroeder, H.R., et al., "Specific Protein Binding . . . ", *Immunoassays: Clinical Laboratory Techniques for the 1980s*, pp. 189–204.

Yaxley, R.E., "The Amerlite . . . ", *Commun. Lab. Med.* (1986).

Hemmilä, I., et al., "Double–Label . . . " *Clin. Chem.*, vol. 33, No. 12, pp. 2281–2283 (1987).

Arnold, L.J., et al., "Assay Formats . . . ", *Clin. Chem.*, vol. 35, No. 8, pp. 1588–1594 (1989).

Weeks, I., et al., "Acridinium Esters . . . ", *Clin. Chem.*, vol. 29, No. 8, pp. 1474–1479 (1983).

Septak, M., "Acridinium Ester–Labelled . . . ", *J. of Bioluminescence and Chemiluminescence*, vol. 4, pp. 351–356 (1989).

VanDyke, K., ed., "Applications of Chemiluminescent . . . ", *Bioluminescence and Chemiluminescence: Instruments and Applications*, vol. I, CRC Press, pp. 23–36 (1985).

DeLuca, M., ed., *Methods in Enzymology*, vol. LVII Academic Press, Inc., pp. 424–445 (1978).

Zomer, G., et al., "Chemiluminogenic . . . ", *Analytica Chimica Acta*, vol. 227, pp. 11–19 (1989).

Weeks et al Clin. Chem. 29/8 1474–1479 (1983) "Acciainian Estes as High–Specific–Activity Labels in Immunoassay".

Jansen et al (1) "HPLC Method for Purification and Quality Control of Isoluminol Labels" in *Luminescence Immunoassay–Molecular Applications* Knox et al ed, CRC Press, pp. 99–118 (1990).

Jansen et al (2) "Horseradish Proxidase as Label in Chemiluminescent Immunoassays" in *Luminescence Immunoassay–Molecular Applications* Knox et al ed, CRC Press, pp. 57–75 (1990).

*Primary Examiner*—Lora M. Green
*Attorney, Agent, or Firm*—Judith A. Roesler; Arthur S. Morgenstern; Robert P. Blackburn

[57] ABSTRACT

A method is provided for detecting or quantitating each of a plurality of substances or at least one substance and an internal reference material or control material in a test sample using at least two different luminescent labelled conjugates. Each luminescent labelled conjugate being characterized in being activated to emit light under different process conditions. The invention also provides for test kits containing at least two different luminescent labelled conjugates for detecting or quantitating presence or absence of at least two substances or at least one substance an internal reference material or control material in a test sample.

38 Claims, 5 Drawing Sheets

ASSAY FOR RGG USING ABEI-RGG

DOUBLE LUMINESCENT ASSAY FOR RGG AND T4

DOUBLE LUMINESCENT ASSAY FOR RGG AND T4

MIXED LUMINESCENT CONJUGATE TEST

This is a continuation of application Ser. No. 08/058,617 filed on May 6, 1993 now abandoned.

TECHNICAL FIELD

The present invention relates to methods for detecting or quantitating each of at least two analytes or an analyte(s) and an internal reference material or a control material in a test sample using at least two different luminescent labelled conjugates. The luminescent conjugates are characterized in that they are activated to emit light by at least two different reaction mechanisms. The invention also provides for test kits containing at least two different luminescent labelled conjugates for detecting or quantitating at least two analytes or an analyte(s) and an internal reference material or a control material in a test sample.

TECHNICAL REVIEW

The detection or quantitation of an analyte in a wide variety of test samples, is provided by assay techniques which rely upon the formation of a complex between the analyte and a corresponding complementary reagent or binding partner. Reagent or binding partner pairing or annealing of an analyte is an integral part of immunoassays, protein-binding assays, nucleic acid hybridization assays, and amplification assays. In typical immunoassays, the analyte may be either an antigen or an antibody and the corresponding binding partner generally is an antibody or antigen, respectively. Various alternate immunoassay or hybridization and amplification techniques and formats thereof are well known in the art.

The test sample containing or suspected of containing the analyte sought to be detected or quantitated may be derived from an industrial or a biological source and may be liquid, e.g., blood or urine, or solid, e.g., tissue biopsy or feces. Control or reference samples are also tested to provide a standard curve to convert the detected amount of the analyte into a quantitated value and for calibration of the instrument.

Assays of the above-stated types have also been used to analyze a wide variety of analytes in test samples in epidemiological and environmental disciplines. In the food industry, for example, such assays have been used to detect toxins and bacterial contamination.

Immunoassays and protein-binding assays may be used to detect or quantitate protein or peptide analytes, therapeutic drugs, and other substances; while nucleic acid hybridization methods may be used to determine the presence or absence of nucleic acid analytes. Like immunoassays, hybridization assays also rely upon the formation of a complex between an analyte and a complementary binding substance. The analyte or target in a hybridization assay is a DNA or RNA having a sequence of bases and the binding substance is a nucleic acid probe capable of binding or annealing to the nucleic acid analyte.

Hybridization assays may be used in connection with a nucleic acid analyte or target having a known or unknown sequence. See U.S. Pat. No. 4,851,336. Thus, hybridization assays are potentially useful for any of the applications discussed with reference to immunoassays and protein-binding assays.

The recent utilization of amplification procedures has further advanced the sensitivity of analytical assays. See U.S. Pat. Nos. 4,683,195 and 4,683,202 describing polymerase chain reaction (PCR) methods and U.S. Pat. Nos. 4,786,660 and 4,957,858 which describe autocatalytic replication of recombinant RNA by QB replicase.

Although each of the above-mentioned assay techniques has in common the specific recognition of an analyte by a corresponding or complementary binding substance to form a detectable complex, the assays may take a variety of formats. Thus, for example, in a direct assay format, a complex is formed between the analyte and its binding partner. Alternatively, in an indirect assay format such as a competitive assay, a complex is formed between a competitor to the analyte and the binding substance. The competitor is characterized by being capable of competing with the analyte for attachment to the binding partner or complementary reagent. Such assay formats and variations thereof are well known in the art and have been extensively published in the technical and patent literature.

In both direct and indirect assay formats, formation of the complex is detected by labeling one or the other member of the complex with a label capable of being detected. Examples of classes of such labels include radioisotopes, e.g., $^{125}I$, $^{3}H$, $^{14}C$, $^{32}P$; enzymes, e.g., horse radish peroxidase; fluorescent compounds, e.g., fluorescein or rhodamine; bioluminescent compounds, e.g., luciferin; and chemiluminescent compounds, e.g., luminol, isoluminol and their derivatives and acridinium esters and benzacridinium esters. However, not all of the above-identified labels are in fact useful. Some labels do not provide adequate sensitivity to detect analytes at their relevant concentrations. To be useful as a label in an immunoassay, a radioisotope must have a sufficiently high radiation energy and decay rate to be detectable at less than picogram quantities, i.e, $10^{-12}$ grams/ml, and at the same time have a sufficiently long half-life that the labelled reagents will have a reasonable shelf life. Disposal, safety issues and short half-lives present problems with the use of radioisotopes. In addition, the labels must have chemical properties such that they can be easily attached to reagents or binding partners or competing without altering the ability of these molecules to undergo their specific binding reactions. Because of these limitations, essentially only one isotope, $^{125}I$, has been widely used in radioimmunoassay (RIA) applications. The absence of a second isotope satisfying these criteria and having a sufficiently different radiation energy spectrum, such that it can be readily distinguished from $^{125}I$ in a mixture, has limited the availability or use of double-label RIA procedures. Programmable liquid scintillation counters have been developed for distinguishing emissions of two radiolabels to address, with some success, the above-stated problem. See U.S. Pat. No. 5,134,294.

Various methods have been published for using two labels in an assay for detection or quantitation of two different analytes. Thus, two different enzymes producing different chromogens or fluorophores can be used as labels, as in the assay of thyroxine and triiodothyronine using alkaline phosphatase and beta-galactosidase. See *Fluorescence Spectroscopy And Its Application To A New Generation of High Sensitivity, Multi-Microspot, Multianalyte, Immunoassay*, Clin Chim Acta, 194, p 91–114, 1990.

Although enzyme labels have avoided many of the problems associated with radioisotopes, enzyme immunoassays are not as sensitive as radioimmunoassays and in general, have a sensitivity limit in the nanograms per milliliter range, i.e., $10^{-9}$ grams/ml. Enzymes also have additional inherent disadvantages as labels, including variability in activity in response to changes in temperature and pH conditions. In addition, enzyme assays require the use of substrates or compounds that react with the enzyme label to produce a detectable product. Many substrates are generally unstable and must be prepared immediately before use. Some substrates are also toxic and one such substrate, ophenylenediamine, is considered carcinogenic.

Luminescent compounds have been used either as substrates in enzyme immunoassays or as labels in luminescent immunoassays. Luminescence refers to the emission of light associated with the dissipation of energy from an electronically excited substance. The different forms of luminescence are distinguished by the mechanism that causes the excitation. In photoluminescence, i.e., fluorescence, the luminescent substance is stimulated by photons of light of a particular wavelength to emit light of a longer wavelength. In bioluminescence, a chemical reaction mediated by enzymes is responsible for the excitation of the luminescent substance. In chemiluminescence, light emission by the luminescent substance is caused by a chemical reaction. See *Bioluminescence and Chemiluminescence, Methods in Enzymology*, Vol LVII, Academic Press, 1978, Chap 37, Monitoring Specific Protein-Binding Reactions with Chemiluminescence; and *Chemiluminescence Labels, Old And New, Anal Chim Acta*, 227, p 11–19, 1989.

A double label assay using fluorescent labels, with each label having emission or absorption maxima at wavelengths sufficiently different to enable easy discrimination, has been used to determine the presence or absence of more than one analyte in a sample. Fluorescent labels are particularly inappropriate for assaying serum samples since many normal protein components of serum are also capable of fluorescing.

Of the chemiluminescent substances, the utility of luminol, as a label in an immunoassay has been limited because its light output upon oxidation is significantly reduced when the label is conjugated to a protein or peptide. N-(4-aminobutyl)-N-ethylisoluminol, an "isoluminol" derivative has been utilized as a label in immunoassays with better results. See U.S. Pat. No. 4,297,273.

Acridinium esters and benzacridinium esters have shown good utility for use in test assays. Acridinium esters are easily oxidized and unlike luminol, the oxidation reaction does not require a catalyst. Moreover, acridinium esters and benzacridinium esters may be conjugated to binding partners and to other molecules without a significant reduction in light emission upon oxidation, and acridinium-labelled assay reagents are generally quite stable in an aqueous environment.

A dual label assay having distinguishable chemiluminescent signals is described in UK 2233450A; where acridinium compounds of varying light emission are utilized and which assays rely on complete emission or emission maxima of one of the compounds in about one second.

These practical limitations help explain the observation that most immunoassays and protein-binding assays have been directed to the detection of a single analyte in a test sample using a single label or label selected from a single class of labels.

SUMMARY OF THE INVENTION

The primary embodiment of the invention provides a method for detecting or quantitating each of at least two substances or at least one substance and an internal reference material or a control material in a test sample, comprising forming a test mixture by admixing said test sample with at least two different luminescent conjugates to form complexes capable of being activated under different process conditions to emit light, and detecting or quantitating each of said substances by applying said different process conditions.

In a multi-substance assay at least two of the process conditions may be the same, so long as the light emission of the process conditions are discernable.

Another embodiment of the invention provides a method of detecting or quantitating each of at least two substances in a sample, comprising forming a test mixture by admixing said test sample with at least two different luminescent conjugates to form complexes capable of being activated under a plurality of process conditions, at least two of the process conditions being distinctive so as to be capable of being carried out in sequence, and detecting or quantitating one of said substances after a first process condition is applied and then detecting or quantitating other of said substances after applying subsequent process conditions.

Another embodiment of the invention provides a method for detecting or quantitating at least two substances in a test sample, comprising the steps of forming a test mixture comprising, said sample containing at least a first substance, and a second substance, a first binding partner capable of specifically attaching to said first substance, a second binding partner capable of specifically attaching to said second substance, a first competitor to said first substance, a second competitor to said second substance, a first luminescent label, said first label attached to one of said first binding partner or said first competitor, and a second luminescent label, said second label attached to one of said second binding partner or said second competitor; allowing said test mixture to react under conditions and for a period of time sufficient to form a first complex comprising, either said first labelled binding partner attached to one of said first substance or the labelled first competitor attached to a binding partner for the first substance, and a second complex comprising either said second labelled binding partner attached to one of said second substance or the labelled second competitor attached to a binding partner for the second substance; detecting or quantitating said first complex and said second complex by activation of said first and second labels by at least two different process conditions wherein said first and second substances are detected or quantitated.

A method is further provided for carrying out a multi-luminescent label assay in which at least one of each of a plurality of luminescent labelled conjugates is bound to at least one analyte, and a light emitted by each of said luminescent labelled conjugates is determined after oxidizing said labels; carrying out oxidizing steps in sequence; and detecting or quantitating the presence or absence or each analyte in response to each of said oxidizing steps.

The invention further provides a kit for detecting or quantitating a plurality of substances in a test sample, comprising at least two different luminescent conjugates, each capable of being activated by a different process condition.

It was found that luminol, isoluminol and their derivatives can be detected at a lower pH than other luminescent labels, i.e. acridinium esters, and this provides for the ability to perform assays using two different luminescent labels.

It is a primary object of this invention to provide a means and method for carrying out the detection or quantitation of a plurality of different substances or at least one substance and an internal reference material or a control material in a single test sample by the use of at least two different luminescent conjugates, the conjugates being activated for detection or quantitation by at least two different process conditions.

Another object of the invention is to provide a kit for detecting or quantitating a plurality of substances in a sample. The kit contains at least two different luminescent labelled conjugates capable of being activated under at least two different process conditions.

According to the invention, a method is provided for detecting or quantitating each of at least two different analytes in a test sample. The method comprises forming a test mixture by mixing the test sample with at least two different luminescent conjugates to form complexes capable of being activated under at least two different process conditions. In a next step, each of the analytes is detected or quantitated by subjecting the test mixture to the different process conditions. In the preferred embodiments, the process conditions include oxidizing conditions which are carried out in sequence. Detection is carried out by measuring emitted light in a light measuring instrument, such as a luminometer, and thereafter quantitating the analyte.

It is an advantage of this invention that by using known luminescent labels, and standard light emission detection equipment a plurality of substances in a test mixture can be detected and quantitated.

It is a further advantage of the invention that by using luminescent labels, sensitivity can be obtained which is at least comparable to that reported for radioisotope assays.

A further advantage of the invention is that the stability of the luminescent compounds and the luminescent conjugates provide a sufficiently long shelf-life to render commercially viable the product of the invention.

These and other objects in view, as will be apparent to those skilled in the art, the invention resides in the combination of elements set forth in the specification and covered by the claims appended hereto.

BRIEF DESCRIPTION OF THE DRAWINGS

The foregoing and other objects and advantages of the invention will be appreciated more fully from the following further description thereof with reference to the accompanying drawings wherein.

DESCRIPTION OF THE PREFERRED EMBODIMENT

Figure 1:
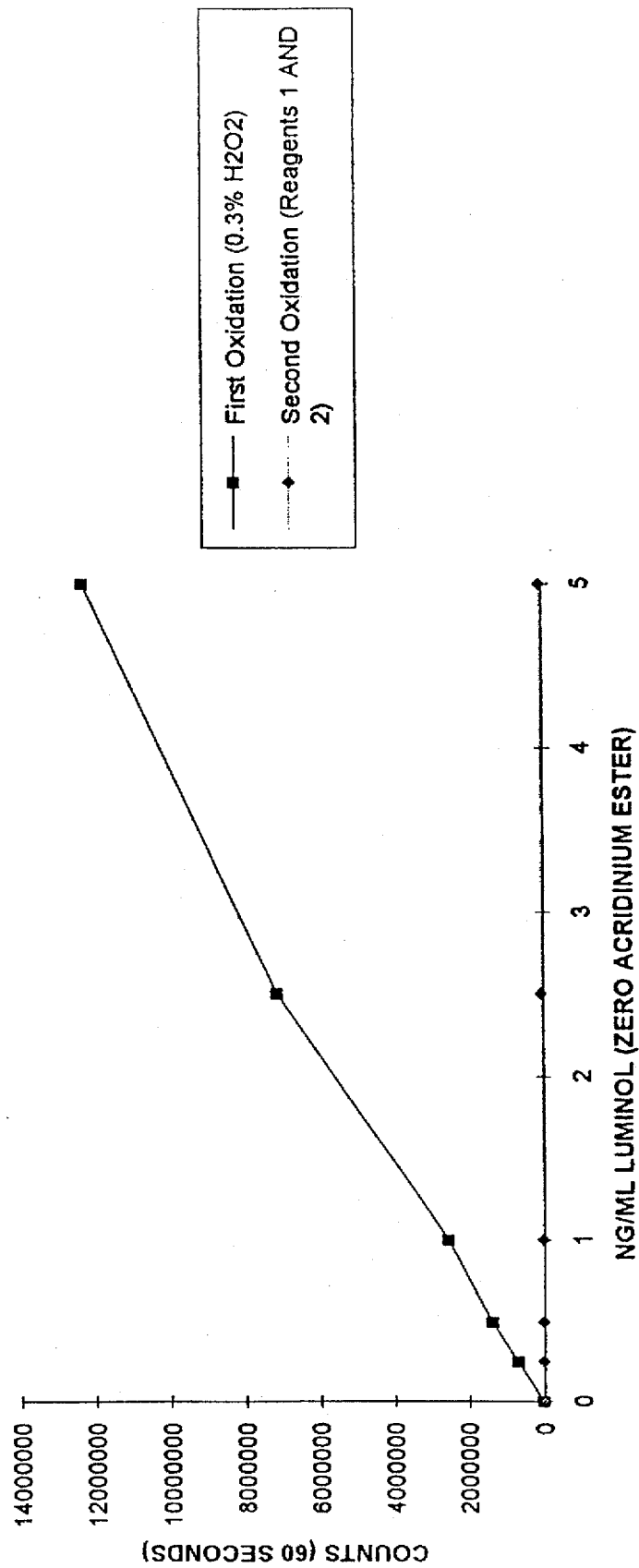
FIG. 1 is a graph of light emission of solutions containing various concentrations of luminol plus a fixed concentration of microperoxidase, on addition of 0.3% hydrogen peroxide and a graph of light emission by luminol, on subsequent addition of Magic Lite Reagents 1 and 2 to the same samples; (Example 1)

In a preferred embodiment, a method is provided for detecting or quantitating each of at least two different substances in a test sample. The sample may be of industrial, biological or other origin and may be liquid or solid. If solid, the sample may be carried in a suitable suspending medium such as water, aqueous-based fluids or organic fluids.

When the test sample is biological, it may be a fluid, e.g., plasma, serum, urine, sputum, whole blood, cerebral spinal fluid, or it may be a solid, e.g., tissue, biopsy material, cells, feces. In some instances, it may be necessary to process or pretreat the sample to make its components suitable for assay. Such process steps may include, for example, homogenization and centrifugation to remove particulate material, base or acid treatment, heat, etc. to access particular substances to be detected or quantitated.

As used herein, the term "substance" refers broadly to any material capable of being detected by formation of a complex with a corresponding complementary reagent or binding partner. Such complex formation is an integral part of various classes of assays, including for example, immunoassays, protein-binding assays, hybridization assays and hybridization steps as part of an amplification assay. Thus, the substance can be one or more of an antigen or antibody in an immunoassay, a protein in a protein-binding assay, or a nucleic acid or nucleic acid probe in a hybridization assay or step and an internal reference material or a control material for use in any of such assays. The internal reference materials and control materials serve to assess the performance of the test method, i.e., for checking against false-positive results. The internal reference materials and control materials are of either known concentration or of known sequence, i.e., in the case of a nucleic acid sequence or amino acid sequence.

As used herein, the term "conjugate" refers to the combination of a label chemically attached to a reagent or binding partner or competitor.

If complex formation constitutes part of an immunoassay, the analyte may be either an antigen or an antibody and the corresponding complementary reagent or binding partner an antibody or antigen, respectively. As used herein, the terms "antigen" or "antigenic analyte" refer broadly to any substance against which antibodies can be produced. The term antigen includes such broad categories of substances as peptides, proteins, nucleic acids and substances formed thereof. Antigenic analytes encompass a diverse spectrum of substances, including antigens, antibodies or derivatives thereof, hormones, haptens, receptors, nucleic acids, nucleic acid probes, toxins, drugs, organic molecules, viruses, and bacteria. A fragment or a derivative of an antibody refers to a portion(s) of the antibody which retains the ability to recognize the epitopes originally recognized by the antibody from which they were derived. The term antibody refers to antibodies produced in vivo or in vitro and includes polyclonal, monoclonal antibody fragments, chimeric antibodies, and other materials produced by recombinant methods, protein splicing techniques, and other methods known in the art.

If complex formation constitutes part of a nucleic acid hybridization assay or step, the analyte is generally a DNA or RNA having a sequence of bases and its complementary reagent or binding partner is a nucleic acid probe which is capable of hybridizing to the nucleic acid analyte. The term "nucleic acid analyte" refers broadly to any nucleic acid having a substantially known sequence against which a complementary nucleic acid probe can be prepared. The sequence of the nucleic acid analyte may be known with certainty, such as by direct nucleic acid sequencing, or may be deduced from a substantially known amino acid sequence for a translation product of the nucleic acid analyte. As used herein, the term "nucleic acid analytes" is not limited to a DNA or RNA which is ultimately translated to a protein product, but also includes non-coding nucleic acid or non-coding nucleic acid sequences within a coding nucleic acid.

To form a test mixture, the sample is mixed with the binding partner for each substance, with each binding partner having attached thereto a different luminescent label. The luminescent labels of the conjugates are capable of being activated to emit light under at least two different process conditions. Alternatively, the test mixture includes a labelled or unlabelled competitor for the substance to be detected in a competitive assay format. A chemiluminescent label is a luminescent substance which is activated to emit light by a specific chemical reaction. Representative chemiluminescent compounds include luminol, isoluminol and their derivatives, acridinium esters and benzacridinium esters. An assay method for two or more substances in a test sample by use of at least one acridinium ester conjugate and at least one benzacridinium ester conjugate is described in U.S. Ser. No. 08/035,130, now U.S. Pat. No. 5,395,752, which is commonly assigned and incorporated herein by reference.

In the assay, each luminescent conjugate becomes bound to a substance to be detected; and in a different format a labelled competitor competes with the substance for specific attachment to the binding partner. When the luminescent conjugate is attached to the substance, the assay is referred to as being in a direct assay format. When the assay includes a labelled competitor to the analyte, the assay is referred to as being in an indirect or competitive assay format. Any of the above-recited classes of assays, e.g., immunoassays, protein-binding assays, hybridization assays, can be designed to be in either a direct or indirect assay format. Since a multi-luminescent conjugate assay detects or quantitates at least two different substances in a single test sample, it is also possible to design a double luminescent assay such that the assay for one substance is in a direct assay format and the assay for the other substance is in an indirect or competitive format.

Luminol, i.e., 5-amino-2, 3, -dihydro-1, 4-phthalazine dione, isoluminol, its variants and derivatives thereof and acridinium esters are well known examples of luminescent compounds. Luminol, isoluminol and their derivatives are activated with a dilute solution of hydrogen peroxide in the presence of a catalyst, such as microperoxidase, to yield an unstable product which emits light as it reverts to a ground state. When the derivative N-(4-aminobutyl)-N-ethylisoluminol is used as a luminescent label, activation results following the addition of 0.05 ml. microperoxidase (10 ug/ml water) and a 0.3% solution of hydrogen peroxide in 0.01M sodium phosphate, pH 7.4. Alternate derivatives may be provided with reactive groups or a spacer arm to provide a compound better suited for conjugation. A spacer arm may include a branched or straight-chained alkyl, substituted or unsubstituted aryl or aralkyl, optionally containing up to 20 heteroatoms.

It was found that luminol, isoluminol and their derivatives can be detected at a lower pH than other luminescent labels, i.e. acridinium esters, and this provides for the ability to perform assays using two different luminescent labels.

Acridinium esters and benzacridinium esters do not require a catalyst for oxidation and are activated to emit light under somewhat different oxidation conditions. In one embodiment, dimethyl acridinium ester (DMAE) (Ciba Corning Diagnostics Corp.) is used as a chemiluminescent label, and activation of the label occurs upon the sequential addition of a 0.5% hydrogen peroxide solution containing 0.1N nitric acid and a 0.25N sodium hydroxide solution containing 0.5% detergent.

In a particular embodiment, each of at least two different substances in a test sample is detected or quantitated by forming a test mixture containing the test sample, binding partners to each substance sought to be detected or quantitated, e.g., analytes including antibodies, with each binding partner having a luminescent label chemically attached thereto. Next, the test mixture is allowed to react under conditions and for a period of time sufficient to form a plurality of complexes. In a preferred embodiment, a first complex comprises an antibody directed against a first analyte, which antibody is labelled. Likewise, the second or another complex comprises the antibody directed against a second analyte, which antibody is labelled. Thereafter, the presence or absence of the analytes, is determined by detecting the luminescent label in each of the complexes.

The above-described embodiments illustrate an immunoassay format in which each of the analytes is an antigen or antigenic analyte. These embodiments are not intended to limit the scope of the present invention. Thus, as would be apparent to one skilled in the art, the present invention also provides for an immunoassay in which each of the analytes is an antibody and the complementary reagent or binding partner is the antigen against which the antibody is directed. Likewise, the invention provides for an immunoassay in which one analyte is an antigen and the second analyte is an antibody. In addition, any of the above-mentioned reagents may be assayed in a direct assay format, or in an indirect competitive assay format.

As would also be apparent to those skilled in the art, modifications of the above-described procedures may be employed to develop additional luminescent labelled binding partners, i.e. luminescent conjugates, or alternate luminescent labels, as well as to develop other classes or formats of assays utilizing the principles of the present invention. Thus, for example, the method of the invention could be used to detect or quantitate least two different genes, at least two different loci on a single chromosome genome, nucleic acid sequence or antibody. Similarly, the method would have application to assays of at least two antibodies of different specificities; assays including at least two antigens; assays including at least one antigen and at least one antibody; and assays for a plurality of molecules indicative of cancer, infectious diseases, genetic abnormalities, genetic disposition, genetic assessment and to monitor medicinal therapy. For example, a first luminescent label could be attached to a nucleic acid probe which specifically binds to one gene and a second luminescent label could be attached to a nucleic acid probe which specifically binds to another or to a different locus on the same gene.

In one embodiment of the present invention the acridinium ester compounds and the benzacridinium ester compounds, depending on which coupling compound is selected, can be reacted directly with the specific binding partner, ligand, or hapten either in an aqueous or an organic medium.

The labels can include an appropriate leaving group or an electrophilic functional group attached with a leaving group or functional groups which can be readily converted into such reactive groups, directly attached or connected via a spacer for attaching a substance to form a conjugate to be utilized in a test assay.

A method for conjugating a luminol derivative to a binding partner is described in U.S. Pat. No. 4,297,273 which is incorporated herein by reference.

A method for conjugating binding partners, haptens, or ligands to polynucleotides is described in EP-A-0 537 994 (priority U.S. Ser. No. 775,399, filed Oct. 16, 1991 now abandoned), which is commonly assigned and incorporated herein by reference.

Thus, N-(4-aminobutyl)-N-ethylisoluminol and dimethyl acridinium ester exemplify in the preferred embodiment a pair of luminescent labels that may be used in a double luminescent labels assay, since each label of the pair is activated to emit light under a different process condition. Process conditions refer to reaction conditions under which the luminescent labels are, for example, activated to an electronically excited state capable of emitting light as it relaxes to a less electronically excited state. As used herein, first process condition refers to the conditions used to activate a first luminescent label. The second process condition refers to the condition used to activate a second luminescent label. In each case, the label is conjugated to a binding partner for the substance to be detected or to a competitor of the substance to be detected depending on the assay format. Additional process conditions may be added for assays testing for more than two substances in a test sample. Such additional process conditions need not be different from the first and second process conditions so long as the light emission of the labels can be distinguished or corrected for where overlap in light emission occurs. Another embodiment of the invention provides for a dual label assay, where the labels include a luminol derivative and an acridinium ester, and the luminol derivative is oxidized by a first process step and the acridinium ester is activated by a second process step.

According to the method of the invention, emitted light is measured after subjecting the test mixture to a first process condition, and again after subjecting the test mixture to a second process condition. In a preferred embodiment, the process conditions are chemically activated oxidation reactions which are carried out in sequence. Appropriate separation steps may be necessary depending on the test assay. Oxidizing conditions may include reaction times of from a millisecond to minutes and temperatures from room temperature to 60° C. Alternate assay formats for testing other substances in a test sample may require reaction times and temperatures beyond or different from those stated herein. In alternate assay methods the process steps, depending on the labels utilized, may be carried out simultaneously and detected simultaneously or sequentially.

Preferably, emitted light is measured after a first oxidizing step and again, after a second oxidizing step. The emitted light is measured using a photomultiplier tube detector device. The detector is preferably equipped with reagent pumps to automatically inject the reagents necessary to activate the first and second labels. A photomultiplier tube detector known as the MAGIC® Lite Analyzer (MLA-1) (Ciba Corning Diagnostics: Corp.) was used to measure emitted light in the below Examples. The MLA-1 is capable of automatically injecting reagents, measuring sample light emission and converting the light emission to analyte concentration by relating sample light emission to the emission of standards containing known amounts of substances in a test sample. A luminometer having a plurality of PMTs is described in U.S. Ser. No. 08/035,341 filed Mar. 19, 1992 now abandoned, which is commonly assigned and is incorporated herein by reference; and which may be utilized in the practice of the present invention.

Selection of an appropriate luminescent label capable of being activated under different process conditions is a prerequisite for developing multi-luminescent label assays. A representative process for the selection of a preferred pair of luminescent labels is disclosed in Example 1. In that experiment, the first luminescent label, luminol, is oxidized to emit light after a first oxidizing step and the second luminescent label, dimethyl methyl acridinium ester, is oxidized to emit light after a second oxidizing step. The experiment showed that the two labels could be discriminated in the presence of one another.

Other luminescent labels may be utilized for such dual label luminescent assays, provided that the pairs of labels are selected such that each member label of the pair is activated to emit light under a different process condition. Examples of alternative chemiluminescent labels which can be used in accordance with the method of the present invention include benzacridinium esters.

A multi-luminescent assay refers to the performance of at least two different luminescent assays in the same vessel or where at least one reaction product(s) or complex is formed in one vessel and is transferred to a second vessel for detection or quantitation or where a first process step is performed in a first vessel and then the contents or a portion thereof are transferred to a second vessel for a second process step. Variations in these process steps may be utilized where multiple substances in a test sample are to be detected or quantitated or where the assay format requires alternate processing and detection steps.

Thus, the present invention provides a more efficient process for detecting the presence or absence of a plurality of different substances in a test sample because it obviates the need for processing a separate test reaction or admixture for each of said substances and where an internal standard material or a control material may be added to the test sample and detected or quantitated in the same assay for at least one substance in the test sample.

Examples 2–5 illustrate the development and execution of a double luminescent label immunoassay for quantitating rabbit gamma globulin (RGG) and thyroxine ($T_4$) in a prepared test sample.

Example 2 describes the preparation of a conjugate of RGG with N-(4-aminobutyl)-N-ethylisoluminol (ABEI) for an RGG immunoassay.

A luminescent immunoassay for RGG, see Example 3, comprises a test mixture including RGG, an ABEI-labelled RGG and a limited amount of immobilized antibody directed against RGG. The test mixture is allowed to react under conditions and for a period of time sufficient to form a complex of either the RGG or the ABEI-labelled RGG to the immobilized antibody. In general, the reaction conditions include vortex mixing the test mixture and allowing the mixture to react for 60 minutes under standard conditions of room temperature, i.e., 20° C., and atmospheric pressure. If RGG is not present in the sample, the complex formed contains a certain amount of the labelled-competitor. If RGG is present in the test sample a portion of that present will bind to the immobilized antibody. Accordingly, the amount of luminescent label present in the complex will be reduced by an amount proportional to the amount of RGG in the sample. The reaction product is next separated in order to quantitate the luminescent conjugate, and hence indirectly the amount of RGG in the sample.

In general, it is desirable to design the assay format such that the complex will be present on a solid phase, for example, by attaching the complementary reagent or binding partner to a solid support or solid phase. In the embodiments disclosed in Examples 3–5, monoclonal antibodies to the antigenic analytes are attached to paramagnetic particles using conjugation methods known in the art, e.g., glutaraldehyde activation. Other solid supports may be utilized in accordance with the methods of the present invention, including latex particles, silica particles, glass particles, cellulose particles, cells, polyacrylamide, agarose, chromatographic support materials, test tubes, microtitre wells and membranes.

Methods are known in the art for separating a test mixture into a liquid and a solid phase fraction.

When paramagnetic particles are used as the solid phase, a magnetic force is used to effect separation in accordance with standard procedures in the art. Next, the solid phase is washed to remove unbound reagents which may have become entrapped in the solid phase during the separation step, i.e., non-specifically bound materials. The washed solid phase is resuspended in a suitable fluid, e.g., distilled or deionized water, and the tubes containing the resuspended solid phase are placed in a detector, e.g., a luminometer, for detection and/or quantitation.

A catalyst, e.g., microperoxidase, is added to the tubes. The catalyst may be added before or after the tubes are introduced to the detector. However, because light emission by the luminescent conjugate is relatively instantaneous upon exposure to an oxidizing solution, the dilute hydrogen peroxide solution, e.g., 0.3 ml of a 0.3% solution of hydrogen peroxide in 0.1M sodium phosphate, pH 7.4, is injected into each tube only after the tube is placed in the detector for light measurement. The amount of analyte present in the sample may be quantitatively determined by relating sample light emission to that of standards containing known amounts of analyte.

A luminescent immunoassay for thyroxine ($T_4$), see Example 4, follows the same general process and conditions as described in reference to the luminescent immunoassay for RGG. The luminescent immunoassay for the determination of $T_4$ may be formatted as a competitive assay in which a dimethyl acridinium ester is conjugated to a $T_4$ competitor. Like the RGG assay, the competitor in the $T_4$ assay is identical to the analyte to be detected.

A chemiluminescent compound, dimethyl acridinium ester, is conjugated to $T_4$ according to standard methods well-known in the art. U.S. Pat. Nos. 4,745,181, 4,918,192, 5,110,932, U.S. Ser. No. 07/826,186 now U.S. Pat. No. 5,227,489 and 07/871,601 now U.S. Pat. No. 5,241,070 describe stable polysubstituted aryl acridinium esters; all of which are commonly assigned and incorporated herein by reference. U.S. Ser. No. 08/035,130, now U.S. Pat. No. 5,395,752 describes benzacridinium compounds and conjugates. The antibody directed against $T_4$ is attached to paramagnetic particles, also using standard methods well-known in the art. As described above in reference to the RGG assay, paramagnetic particles serve as a solid phase to facilitate separation of the detectable reaction product(s) or complex. Such separation is necessary to ultimately detect the luminescent conjugate in a complex, thereby detecting or quantitating the substance(s) in the test sample.

After washing the separated fraction to remove soluble reagents which may have become entrapped in the separated fraction during the separation step, the separated fraction is resuspended in a suitable fluid, e.g., distilled water, and the tubes containing the resuspended separated fraction are placed in a detector. In some assay formats, washing may not be necessary, as simple decanting may suffice. Because the light emission of the acridinium ester label is relatively instantaneous following the addition of Reagent 1 (0.5% hydrogen peroxide, 0.1N nitric acid) and Reagent 2 (0.25N sodium hydroxide, 0.5% detergent), these two reagents are automatically injected into each tube after the tube has been properly positioned in the detector for measurement of emitted light.

In the dual label luminescent immunoassay of the present invention, see Example 5, the immunoassay for RGG, Example 3, is combined with the immunoassay for $T_4$, Example 4, and the two assays are performed in a single vessel. The dual luminescent label assay uses the ABEI-labelled RGG of Example 3, and the dimethyl acridinium ester-labelled RGG of Example 4, as first and second luminescent conjugates which, after the test reaction, are activated to emit light under first and second process conditions. The first luminescent label is not limited to the isoluminol derivative ABEI of Example 3, but may be a derivative or variant of luminol or any other luminescent label, as long as the variant or other label is capable of being activated to emit light under reaction conditions which differ from those conditions required for activation of the second luminescent label. In general, the assay conditions for the dual luminescent label assays are the same as those of single label assays, with minor variations. Accordingly, the test mixture of the dual assay is allowed to react for 60 minutes under standard conditions of room temperature. Reaction conditions may be varied, however, to decrease or increase the reaction time.

Next, the test mixture is separated into a liquid phase and a solid phase. In general, separation is effected by magnetic particles to which are attached the reaction complexes. However, one or more of any of the above-recited solid supports and methods may be used to separate the test mixture of the double label assay into one or more soluble and insoluble fractions. The solid phase fraction is washed to remove unbound reagents or substances which may have become entrapped in the insoluble fraction during the separation step. Thereafter, the washed insoluble fraction is resuspended in a suitable fluid, e.g., distilled or deionized water, and the catalyst required for the oxidation of luminol, isoluminol or derivatives thereof, is added to the tubes. The tubes are then placed in a photomultiplier tube detector device, i.e., a luminometer, which is capable of sequentially injecting the reagents to activate the first and second chemical process conditions. In a preferred embodiment, the first chemical process condition is the oxidation reaction for the activation of the isoluminol derivative label of Example 3, and the second chemical reaction is the oxidation reaction for the activation of dimethyl acridinium ester label, as described in Example 4.

The detection of the first luminescent label in the first complex indicates the presence or absence of the first substance in the sample depending on the assay format. Likewise, the detection of the second luminescent label in the second complex indicates the presence or absence of the second substance in the sample depending on assay format, where said second substance may include an internal reference material or control material. The amount of substance in a test sample can be quantitatively determined by relating sample light output to that of standard samples containing known amounts of substances or, by comparison, with a control material, if appropriate.

A theoretical dual luminescent label assay is shown in Example 6 to illustrate the potential clinical utility of the method of the invention. The theoretical assay describes the determination of luteinizing hormone (LH) and follicle stimulating hormone (FSH) contained in a serum sample.

In addition to the above-disclosed methods and examples, the invention provides a kit for detecting or quantitating at least two analytes in a test sample. The kit comprises at least two different luminescent labels each of which is conjugated to a binding partner for a substance to be detected in the test sample or at least one labelled or unlabelled competitor for a substance to be detected in the test sample, depending on assay format to form a complex capable of being activated under at least two different reaction conditions.

The kits may be used to detect or quantitate a plurality of substances, including antigens, antibodies, hormones, haptens, receptors, nucleic acids, nucleic acid probes, toxins, organic chemicals, drugs, and infectious agents. For each substance, the kit may contain at least one labelled complementary reagent or binding partner, or a labelled or unlabelled competitor of the substance to be detected depending on the assay format. In one of the preferred embodiments, the analytes are antigens and the reagents or binding partners are antibodies. In yet another embodiment, the analytes are nucleic acids and the reagents or binding partners are nucleic acid probes, capable of binding to the nucleic acid analytes.

The following Examples are illustrative of the invention but should not be considered as limiting the scope of the invention. Described in Example 1 is the experimental discrimination between two luminescent labels by two different process conditions. Example 2 shows a preferred method for the conjugation of an isoluminol derivative label to RGG. Example 3 illustrates a luminescent label immunoassay for the determination of a single analyte. Example 4 illustrates a luminescent label immunoassay for the determination of a single analyte ($T_4$). Described in Example 5 is a dual luminescent conjugate immunoassay for the determination of two different analytes in accordance with the method of the invention. Example 6 illustrates a theoretical dual luminescent label immunoassay for the determination of FSH and LH.

EXAMPLE 1

DEMONSTRATION OF INDEPENDENT DETECTION OF TWO LUMINESCENT COMPOUNDS

Luminescent Compounds

Solutions of 5-amino-2,3-dihydro-1,4-phthalazinedione (luminol) at known concentrations as shown in Table 1 in the range 0.25–5.0 ng/ml in PBS/BSA (0.1M sodium phosphate, pH 7.4, 0.15M sodium chloride, 1 mg/ml bovine serum albumin) were prepared by dilution from a stock solution of 0.5 mg/ml of the compound in methanol. Standard solutions of DMAE (dimethyl acridinium ester) at known concentrations as shown in Table 1 were made by dilution of a stock solution of DMAE-NHS (2,6-dimethyl-4-)2-succinimidyloxycarbonylethyl)-phenyl-10-methyl acridinium-9-carboxylate fluorosulfonate) in DMF (dimethyl formamide) (153 ug/ml) to a concentration in the range of 0.25–10.0 ng/ml with PBS/BSA.

Light Measurement

All measurements were made in a standard Ciba Corning MLA-1 Magic Lite Analyzer. To determine the concentration of luminol, a 0.3% hydrogen peroxide solution was injected. To determine the dimethyl acridinium ester concentration, Reagent 1, followed by Reagent 2, were added.

Preparation of Luminescent Samples

Figure 2:
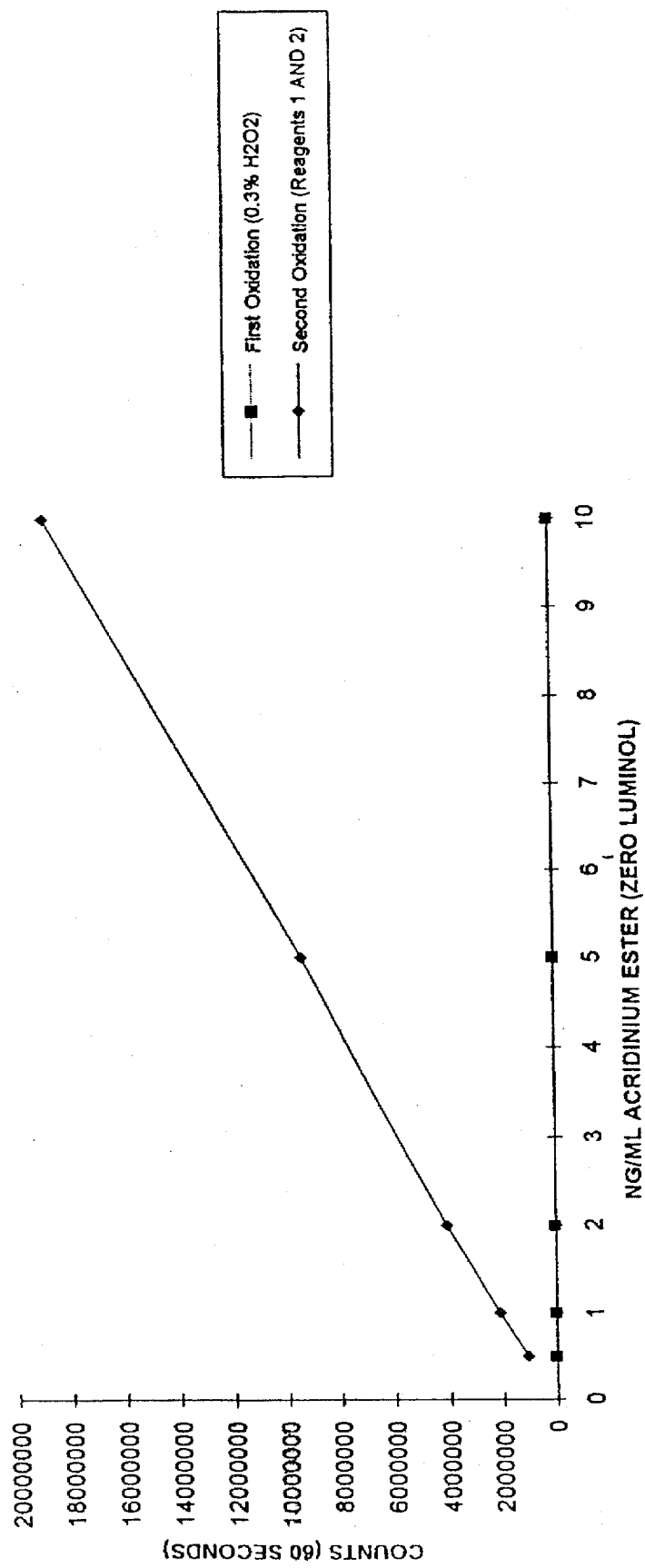
FIG. 2 is a graph of light emission by solutions containing various concentrations of DMAE, plus a fixed concentration of microperoxidase, on addition of 0.3% hydrogen peroxide; and a graph of light emission by DMAE, on subsequent addition of Magic Lite Reagents 1 and 2 to the same samples (Example 1)

Sets of samples (0.2 ml), containing various concentrations of luminol alone, dimethyl acridinium ester alone, or a mixture of luminol and the dimethyl acridinium ester, were placed in polystyrene tubes. To each sample (at room temperature) was added 0.05 ml microperoxidase (MP-11, Sigma Chemical Corp., 10 ug/ml in water) to catalyze the light emitting oxidation of luminol. All samples were then placed in the MLA-1 and oxidized upon injection of 0.3 ml 0.3% hydrogen peroxide. The light generated in each sample tube was measured for 60 seconds. The reagents in the MLA-1 were then changed to Reagent 1 (0.5% to hydrogen peroxide plus 0.1N nitric acid) and Reagent 2 (0.25N sodium hydroxide, plus surfactant) (Ciba Corning Diagnostics Corp.). The same samples were oxidized a second time by sequentially injecting Reagent 1 and Reagent 2 and the light generated was again measured for 60 seconds. The total counts of emitted light for each sample tube were recorded and are shown in Table 1. The results are also depicted graphically in FIG. 1 (luminol emission) and in FIG. 2 (acridinium ester emission).

TABLE 1

LUMINESCENCE OF LUMINOL AND ACRIDINIUM ESTER MIXTURES

| Conc. (ng/ml) | | Counts (60 seconds) | |
|---|---|---|---|
| Luminol | Acridinium Ester | First Oxidation (0.3% $H_2O_2$) | Second Oxidation (Reagents 1 and 2) |
| 0 | 0 | 37030 | 14750 |
| 0.25 | 0 | 708800 | 18360 |
| 0.5 | 0 | 1380650 | 21650 |
| 1.0 | 0 | 2563010 | 29240 |
| 2.5 | 0 | 7145260 | 55740 |
| 5.0 | 0 | 12290630 | 75010 |
| 0 | 0.5 | 36290 | 1090150 |
| 0 | 1.0 | 37080 | 2118340 |
| 0 | 2.0 | 37650 | 4091630 |
| 0 | 5.0 | 39720 | 9402260 |
| 0 | 10.0 | 40850 | 18828160 |
| 0.125 | 5.0 | 369940 | 9939740 |
| 0.25 | 2.5 | 709910 | 4929400 |
| 0.5 | 1.0 | 1334770 | 2090000 |
| 1.25 | 0.5 | 3148700 | 1068000 |
| 2.5 | 0.25 | 6137300 | 578320 |

Referring to Table 1, light emitted (expressed as counts/60 seconds) following the first oxidation, i.e., first chemical process condition, was directly proportional to the concentration of luminol. The results also demonstrate that the presence of acridinium ester at concentrations as high as 10 ng/ml did not interfere with the luminol measurement, i.e., acridinium ester did not emit a significant amount of light during the first process condition. Similarly, the counts of light emitted following the second process condition, were proportional to the concentration of acridinium ester in the mixture. The presence of luminol at concentrations up to 5 ng/ml contributed a small fraction of the counts generated following the first process condition. The contribution to emitted light by luminol following the second oxidation represented only about 0.5% of the counts generated following the first process condition if background counts, i.e., light emitted at 0 ng/ml luminol, were subtracted prior to the determination of percentages. These results demonstrate the feasibility of measuring luminol or a related compound and dimethyl acridinium ester labels accurately and independently in the same sample mixture using different process conditions. Similar experiments may be carried out in testing the feasibility of uses of other paired or multi-luminescent label assays.

EXAMPLE 2:

CONJUGATION OF ISOLUMINOL DERIVATIVE TO RABBIT GAMMA GLOBULIN

A method for conjugating an isoluminol derivative label to rabbit gamma globulin (RGG) is provided herein.

Activation

Five milligrams of N-(4-aminobutyl)-N-ethylisoluminol (ABEI) were added to 1 ml of DMF (dried over molecular sieves). To this were then added 2.2 mg of succinic anhydride in 0.06 ml of DMF, followed by 1.8 mg of triethylamine in 0.1 ml of DMF.

The mixture was heated at 70° C. for 1.5 hours, to give a clear solution. The solution was cooled, and to it were added 3.7 mg of dicyclohexylcarbodiimide in 0.025 ml of DMF and 2.5 mg of N-hydroxy-succinimide in 0.025 ml DMF. This "activated ABEI solution" was then stored for 2 days at about 4° C.

Coupling

Two milligrams of RGG were dissolved in 1 ml of 0.1M carbonate/bicarbonate buffer, pH 9, and 0.1 ml of the activated ABEI solution was added, with vortexing. The mixture was left at room temperature for 2 hours, then stored overnight at about 4° C.

The conjugate was separated from unconjugated ABEI on a PD-10 gel filtration column prepacked with Sephadex G25, (Pharmacia) and eluted with PBS (sodium phosphate, 0.15M sodium chloride, pH 7.4). Fractions containing the initial peak of luminescent material were combined for use in the luminescent immunoassay for RGG, described in Example 3.

EXAMPLE 3

LUMINESCENT ASSAY FOR RABBIT GAMMA GLOBULIN

To polystyrene tubes containing 50 ul of known concentrations of RGG as shown in Table 2 in the range of 2.5 to 200 ug/ml (diluted in PBS/BSA) (PBS containing 1 mg bovine serum albumin per ml) (including a zero RGG PBS/BSA tube) was added an equal volume of ABEI-RGG tracer, diluted in PBS/BSA, to give approximately $5 \times 10^5$ unquenched counts. One hundred microliters of antibody directed against RGG (MAb-anti RGG), coupled to paramagnetic particles by glutaraldehyde activation, was then added to each tube. In the preferred embodiment, the antibody solution was prepared by diluting a 10 mg/ml stock suspension of antibody coupled particles up to 1:50 with PBS/BSA. Reaction tubes were vortexed and incubated for 1 hour, at room temperature. Thereafter, a three minute magnetic separation was performed, followed by decantation. The solid phase fraction, was then resuspended in 1.0 ml of water, separated for 3 minutes, and decanted for 3 minutes. Next, 100 microliters of water was added to the reaction tubes containing the solid phase fraction.

Fifty microliters of microperoxidase (MP-11, Sigma, 10 ug/ml in water) was added to each tube. All tubes were then transferred to a detector (MLA-1), and 0.3 ml of 0.3% hydrogen peroxide in 0.01M sodium phosphate pH 7.4 was injected into each tube, and the light emitted in each tube was measured for 10 seconds. The counts bound, i.e., counts of light attributed to the ABEI-labelled RGG which was bound to the solid phase are shown in Table 2.

TABLE 2

| Assay for RGG Using ABEI-RGG | |
|---|---|
| RGG ug/ml | Counts Bound (C.B.) |
| 0.0 | 41,995 |
| 2.5 | 38,700 |

TABLE 2-continued

| Assay for RGG Using ABEI-RGG | |
|---|---|
| RGG ug/ml | Counts Bound (C.B.) |
| 5.0 | 33,420 |
| 10.0 | 28,210 |
| 25.0 | 21,835 |
| 50.0 | 15,885 |
| 100.0 | 13,045 |
| 200.0 | 11,300 |

Figure 3:
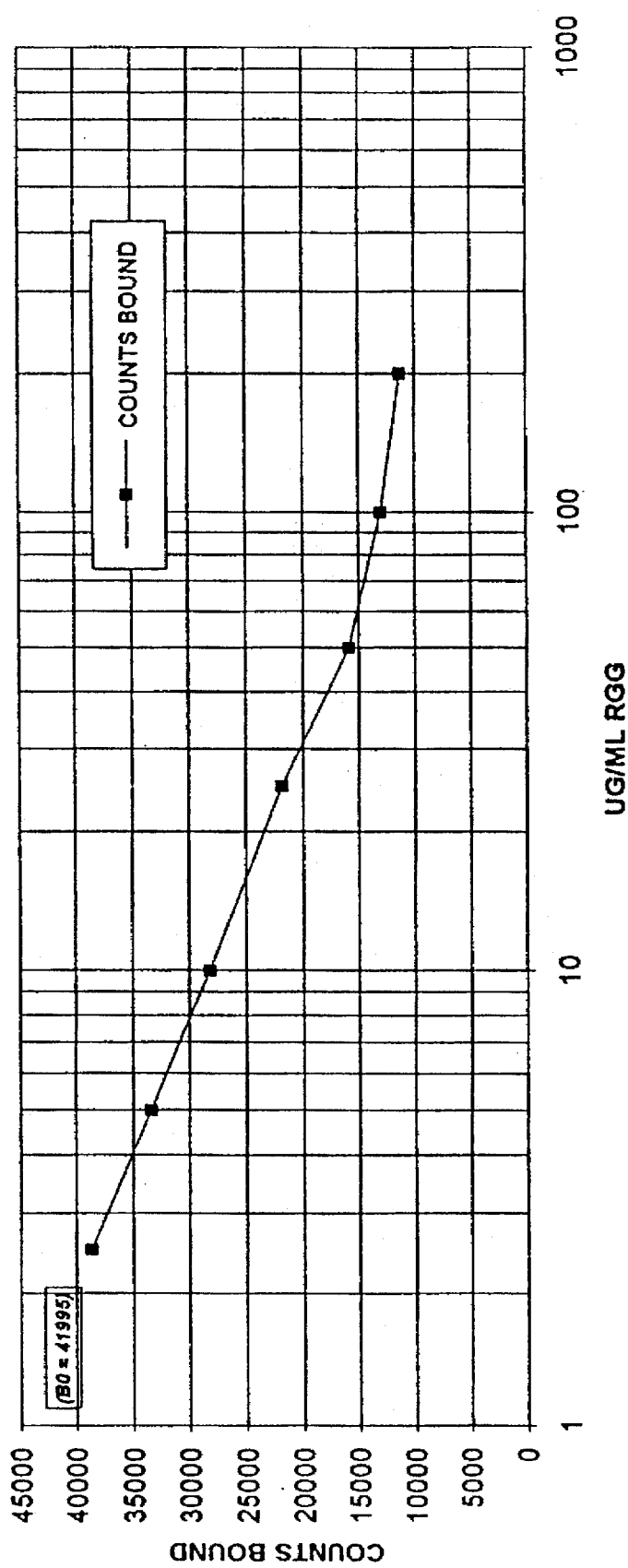
FIG. 3 is a standard curve for determination of RGG in accordance with the luminescent label assay of the present invention (Example 3)

As can be seen from Table 3 and FIG. 3, the addition of as little as 2.5 ug/ml of RGG, equivalent to 125 ng or 0.833 pmol of RGG, was detectable by reduction of the amount of ABEI labelled RGG bound to the solid phase.

EXAMPLE 4

LUMINESCENT ASSAY FOR $T_4$

The luminescent assay for $T_4$ is based on a version of the Magic Lite $T_4$ assay kit sold by Ciba Corning Diagnostics Corp., modified for the purpose of this example. The modification consists of the use of a range of $T_4$ standards, 0.5 to 50 ug/dl, in PBS/BSA, instead of the two serum-based standards supplied in the kit. The other reagents used in the example are those supplied in the kit, i.e., a suspension of a monoclonal antibody to $T_4$, attached to paramagnetic particles (MAb-anti-$T_4$ PMP), and a dimethyl acridinium ester $T_4$.

The $T_4$ assay, when performed on its own, uses the following procedure: To polystyrene tubes containing 50 ul of the sample to be assayed, or of a $T_4$ standard solution, is added 100 ul of dimethyl acridinium ester $T_4$, diluted in PBS/BSA to give approximately $5 \times 10^5$ counts. Five hundred microliters of the paramagnetic particles is then added to each tube. The reaction tubes are vortexed and incubated for 60 minutes at room temperature. During this time, the antibody binds to the analyte $T_4$ or the acridinium ester $T_4$.

Separation of the test mixture into a soluble fraction and an insoluble fraction is as described in Example 3. The pellet of insoluble antibody, with the bound analyte or labelled analyte, is then resuspended in 1 ml of water to wash off any unbound label. The antibody containing particles are again collected in the magnetic field for 3 minutes, and the water decanted and discarded. Finally, the particles are resuspended in 100 ul of water and transferred to the MLA-1 for performance of the oxidation reaction and measurement of emitted light.

The MLA-1 is programmed to automatically inject Reagent 1 and Reagent 2 which comprises a process condition as described herein. Reagent 1 is injected first, followed by Reagent 2. The light emitted in each tube is measured for 2 seconds. The counts recorded, representing acridinium ester labelled $T_4$ bound to the antibody, have an inverse relationship to the $T_4$ in the sample.

EXAMPLE 5

DUAL LUMINESCENT LABEL ASSAY FOR RABBIT GAMMA GLOBULIN AND $T_4$

A dual label luminescent immunoassay refers to the performance of two luminescent immunoassays in the same vessel. In this example, the isoluminol-based assay for RGG antigen was combined with the acridinium ester-based assay for $T_4$ antigen.

The reagents for the dual luminescent label immunoassay were added to polystyrene tubes in the following order: the RGG standards and ABEI-labelled RGG, the $T_4$ standards and the acridinium ester $T_4$, and the two insoluble antibodies bound to paramagnetic particles. The tubes were vortexed, incubated for 60 minutes, and the paramagnetic particles were then separated, washed, and resuspended as described in reference to the individual assays for RGG and $T_4$. Fifty microliters of 10 ug/ml microperoxidase were added to each tube. Thereafter, the tubes were placed in the MLA-1 and 0.3 ml of 0.3% hydrogen peroxide solution was injected into each tube. The light emitted upon the oxidation of the ABEI-labelled RGG was collected for 10 seconds. Reagent 1, followed by Reagent 2 were then injected to the same set of tubes. The light emitted by the dimethyl acridinium $T_4$ upon exposure to Reagent 1 and Reagent 2 was collected for 10 seconds.

The results shown in Table 3 demonstrate that assay sensitivity for the RGG analyte in the combined dual luminescent label immunoassay was approximately equivalent to that observed for the single RGG assay of Example 3. Likewise, assay sensitivity for the $T_4$ analyte in the combined $T_4$ dual luminescent label immunoassay was about the same as that reported for the single $T_4$ assay of Example 4.

TABLE 3

Double Luminescent Assay For RGG and $T_4$

| First Process Conditions 0.3% $H_2O_2$ | | Second Process Conditions Reagents 1 & 2 | |
|---|---|---|---|
| RGG ug/ml | Counts | $T_4$ ug/dl | Counts |
| 0.0 | 11015 | 0.0 | 242770 |
| 2.5 | 9192 | 0.5 | 205795 |
| 5.0 | 8515 | 1.0 | 168950 |
| 10.0 | 7510 | 2.5 | 92520 |
| 25.0 | 6450 | 5.0 | 52570 |
| 50.0 | 5785 | 10.0 | 30925 |
| 100.0 | 5870 | 25.0 | 17830 |
| 200.0 | 5360 | 50.0 | 15195 |

The dual luminescent assay for RGG and $T_4$ was used to determine the concentrations of RGG and $T_4$ in a set of simulated "unknown" mixtures containing RGG and $T_4$ at known concentrations. As shown in Table 4, the relative concentrations of $T_4$ and RGG were selected to maximize assay interference by one analyte in the determination of the other analyte, i.e., low concentrations of one analyte were determined in the presence of high concentrations of the other analyte.

TABLE 4

Mixture of "Unknowns"

| | | Counts Bound | |
|---|---|---|---|
| | | First Oxidation | Second Oxidation |
| A. | 25 ug/ml RGG plus 0.5 ug/dl $T_4$ | 6530 | 198295 |
| B. | 10 ug/ml RGG plus 1.0 ug/dl $T_4$ | 7380 | 172075 |
| C. | 5.0 ug/ml RGG plus 5.0 ug/dl $T_4$ | 8395 | 96420 |
| D. | 2.5 ug/ml RGG plus 5.0 ug/dl $T_4$ | 9725 | 53050 |

Figure 4:
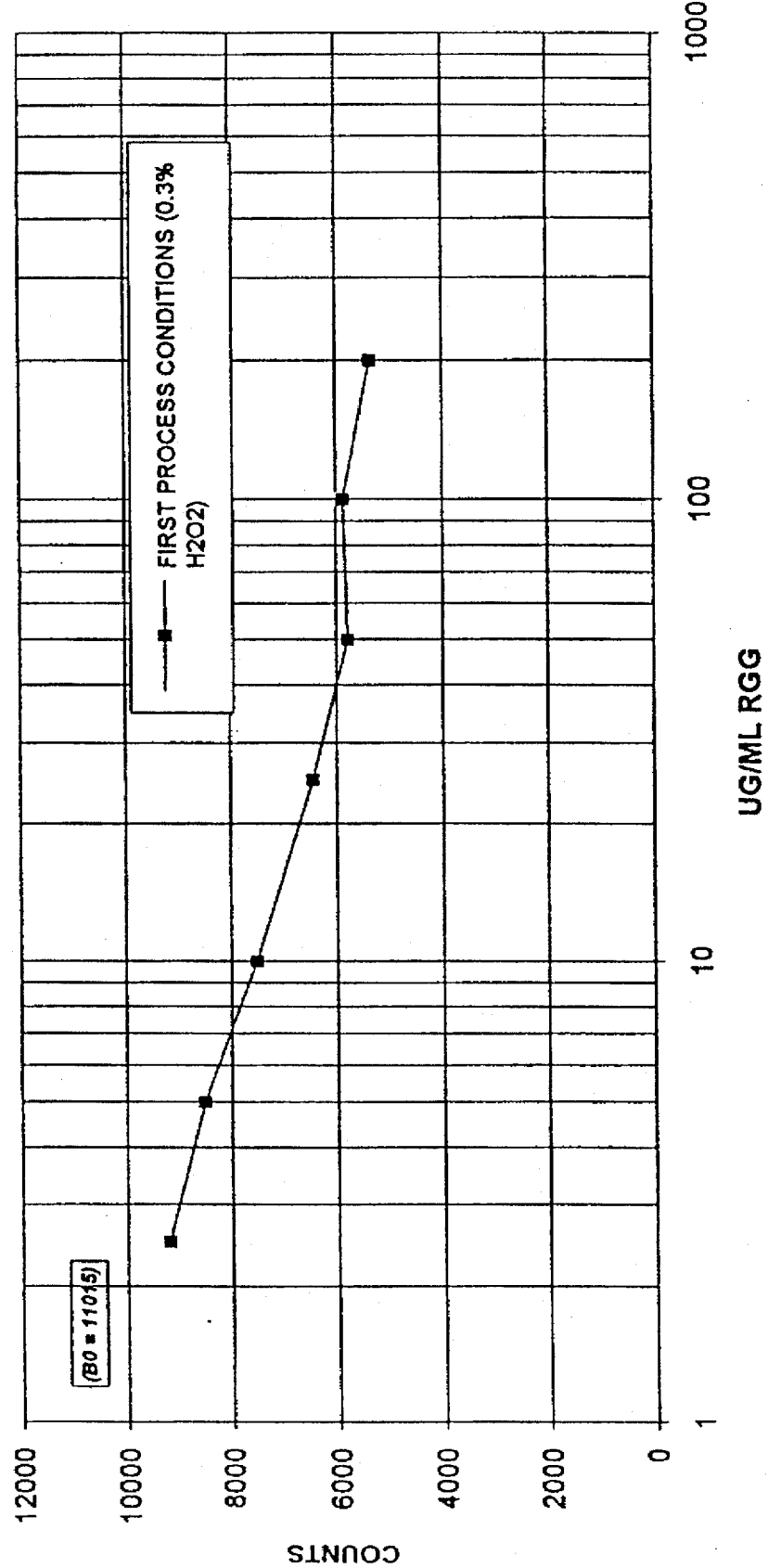
FIG. 4 is a standard curve for determination of RGG in accordance with the double luminescent label immunoassay (Example 5)
Figure 5:
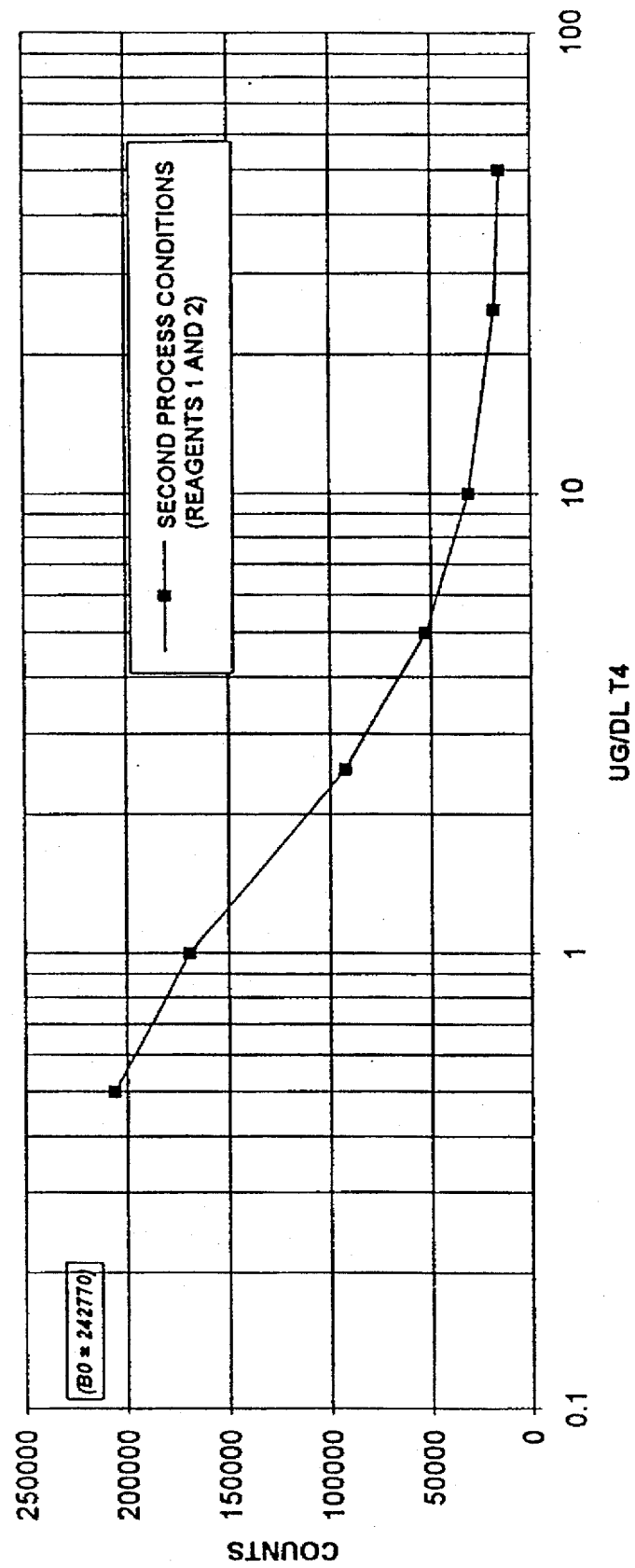
FIG. 5 is a standard curve for determination of $T_4$ in accordance with the double luminescent label immunoassay (Example 5).

The amounts of each analyte in the "unknown" mixtures were determined using the standard curves generated for each analyte in the double luminescent label assay (FIG. 4 shows the standard curve obtained for RGG; FIG. 5 shows the standard curve obtained for $T_4$). The experimentally determined concentrations of each analyte are compared to the known concentrations in Table 5.

TABLE 5

Determination of RGG and $T_4$ Concentrations Using the Dual Luminescent Conjugate Assay

| | First Oxidation (0.3% $H_2O_2$) (ug/ml RGG) | | Second Oxidation (Rgts. 1&2) (ug/dl $T_4$) | |
|---|---|---|---|---|
| | Expected | Obtained | Expected | Obtained |
| A. | 25.0 | 25.0 | 0.5 | 0.6 |
| B. | 10.0 | 10.8 | 1.0 | 0.95 |
| C. | 5.0 | 5.0 | 2.5 | 2.45 |
| D. | 2.5 | 1.95 | 5.0 | 5.0 |

The results shown in Table 5 demonstrate that the dual luminescent conjugate assay accurately and independently measured two separate analytes in the same assay tube.

EXAMPLE 6

SIMULTANEOUS ASSAY FOR LUTEINIZING HORMONE (LH) AND FOLLICLE STIMULATING HORMONE (FSH)

An aliquot (for example 100 ul) of the sample containing LH and FSH, the concentrations of which are to be determined, is mixed with a volume (for example 100 ul) of a buffer solution containing an antibody to LH labelled with DMAE, as well as an antibody to FSH labelled with an isoluminol derivative, e.g., ABEI. The mixtures are allowed to incubate for a period of time (for example 30 minutes), during which the labelled antibodies combine with the LH and FSH. A volume of buffer (for example 500 ul) containing a quantity of magnetic particles having antibody to LH attached, as well as a quantity of magnetic particles having antibody to FSH attached, is then added. A further incubation period (for example 30 minutes) then occurs, during which the complexes of LH and FSH with their respective labelled antibodies are bound in turn by the corresponding antibodies on the magnetic particles. The magnetic particles are then collected at the bottom of the incubation tube by the application of a magnetic field, and the supernatant liquid is decanted and discarded. The particles are washed by resuspension in water, and collected again by the magnetic field. The supernatant wash fluid is decanted and discarded.

The particles are resuspended in a small volume of water (for example 100 ul), to which is added a solution of microperoxidase (for example 50 ul of a 10 ug/ml solution). The reaction tubes are then placed in turn in the luminometer. Hydrogen peroxide (0.3% in phosphate buffer, pH 7.4) is injected, and the emitted light measured for several seconds (for example 5 seconds). This measurement represents the amount of isoluminol labelled FSH antibody bound to the magnetic particles, and is therefore related to the amount of FSH in the sample. Next, into the same tubes, Reagent 1 and Reagent 2 are injected sequentially, followed again by measurement of the emitted light. This second measurement represents the amount of DMAE labelled LH antibody bound to the particles, and is therefore related to the amount of LH in the sample. The amount of luminescent label quantitated will be reduced by an amount proportional to the amount of LH or FSH in the sample.

The actual concentrations of FSH and LH in the unknown sample are computed by reference to the amounts of light emitted from standards containing known amounts of FSH and LH, which have been subjected to the same assay procedure.

It is to be understood that various other modifications will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given therein are intended to illustrate, and not to limit the invention.

What is claimed is:

1. A dual luminescent label specific binding assay for detecting two substances in a sample comprising the sequential steps of:
   (a) forming a test reaction mixture comprising:
      (i) a test sample comprising a first substance and a second substance;
      (ii) a first test reagent comprising a first binding partner (BP1) which specifically binds to said first substance wherein said first binding partner is attached to a first luminescent label selected from the group consisting of luminols and isoluminols ($BP1_L$) and a second binding partner (BP2) which is immobilized on a solid support ($BP2_S$); and
      (iii) a second test reagent comprising a third binding partner (BP3) which specifically binds to said second substance wherein said third binding partner is attached to a second luminescent label selected from the group consisting of acridinium esters and benzacridinium esters ($BP3_L$) and a fourth binding partner (BP4) which specifically binds to said second substance, wherein said fourth binding partner is immobilized on a solid support ($BP4_S$);
   (b) reacting said test mixture to form a first specific binding complex comprising $BP1_L$-first substance-$BP2_S$, and a second specific binding complex comprising $BP3_L$-second substance-$BP4_S$;
   (c) separating said first and second binding complexes from unbound $BP1_L$ and $BP3_L$;
   (d) activating said first luminescent label in the presence of an oxidation catalyst at a first pH process condition to emit a first measurable light emission from said first luminescent label, wherein said first pH process condition does not activate said second luminescent label;
   (e) measuring said first light emission;
   (f) activating said second luminescent label at a second pH process condition to emit a second measurable light emission from said second luminescent label;
   (g) measuring said second light emission; and
   (h) correlating the first light emission to the presence or amount of said first substance and correlating the second light emission to the presence or amount of said second substance present in said test sample,
   wherein said first pH condition is a pH level lower than said second pH condition.

2. A method according to claim 1 wherein said first and second binding partners are antibodies which bind to said first substance, wherein said first substance is an antigen, and said third and fourth binding partners are antibodies which bind to said second substance, wherein said second substance is an antigen.

3. A method according to claim 2 wherein said first luminescent label is selected from the group consisting of N-(4-aminobutyl)-N-ethylisoluminol and 5-amino-2,3-dihydro-1,4-phthalazine dione and said second luminescent label is dimethyl acridinium ester.

4. A method according to claim 1 wherein said first pH condition is 7.4.

5. A method according to claim 1 wherein said first label is N-(4-aminobutyl)-N-ethylisoluminol and said second label is a dimethyl acridinium ester and said second label is activated upon the sequential addition of a first solution comprising hydrogen peroxide and nitric acid followed by a second solution comprising sodium hydroxide.

6. A method according to claim 5 wherein said first label is activated with an activating agent comprising hydrogen peroxide in the presence of a microperoxidase catalyst.

7. A dual luminescent label specific binding assay for detecting two substances in a sample comprising the sequential steps of:
   (a) forming a test reaction mixture comprising:
      (i) a test sample comprising a first substance and a second substance;
      (ii) a first test reagent comprising a first binding partner (BP1) which of specifically binds to said first substance and a first competitor (C1) which competes with said first substance for binding to said first binding partner, wherein said first binding partner is immobilized on a solid support ($BP1_S$) and said first competitor to said first substance is attached to a first luminescent label selected from the group consisting of luminols and isoluminols ($C1_L$);
      (iii) a second test reagent comprising a second binding partner (BP2) which specifically binds to said second substance and a second competitor (C2) which competes with said second substance for binding to said second binding partner wherein said second binding partner is immobilized on a solid support ($BP2_S$) and said second competitor to said second substance is attached to a second luminescent label selected from the group consisting of acridinium esters and benzacridinium esters ($C2_L$),
   (b) reacting said test mixture to form a first specific binding complex comprising either $BP1_S$-first substance or $BP1_S$-$C1_L$, and a second specific binding complex comprising either $BP2_S$-second substance or $BP2_S$-$C2_L$;
   (c) separating said first and second complexes from said unbound $C1_L$ and $C2_L$;
   (d) activating said first luminescent label in the presence of an oxidation catalyst at a first pH process condition to emit a first measurable light emission wherein said first pH process condition does not activate said second luminescent label;
   (e) measuring said first light emission;
   (f) activating said second luminescent label at a second pH process condition to emit a second measurable light emission;
   (g) measuring said second light emission; and
   (h) correlating the first light emission to the presence or amount of said first substance and correlating the second light emission to the presence or amount of said second substance present in said test sample,
   wherein said first pH condition is a pH level lower than said second pH condition.

8. A method according to claim 7 wherein said first luminescent label is selected from the group consisting of N-(4-aminobutyl)-N-ethylisoluminol and 5-amino-2,3-dihydro-1,4-phthalazine dione.

9. A method as recited in claim 8, wherein said first and second substances are selected from the group consisting of antigens, antibodies, haptens, hormones, receptors, nucleic acids, nucleic acid probes, toxins, organic chemicals, drugs, infectious agents, internal reference materials and control materials.

10. A method as recited in claim 9, wherein said first label is activated at a pH condition of 7.4.

11. A method as recited in claim 8, wherein said first luminescent label is N-(4-aminobutyl)-N-ethylisoluminmol and said second label is dimethyl acridinium ester, wherein said first label is activated by addition of a microperoxidase oxidation catalyst in the presence of a hydrogen peroxide solution and said second label is activated upon the sequential addition of a first solution comprising hydrogen peroxide and a nitric acid followed by a second solution comprising sodium hydroxide.

12. A dual luminescent label specific binding assay for detecting a substance and an internal reference material comprising the sequential steps of:
(a) forming a test reaction mixture comprising:
(i) a test sample comprising a substance to be detected or quantitated;
(ii) a first test reagent comprising a binding partner which specifically binds to said substance and a competitor which competes with said substance for binding to said binding partner wherein said binding partner is immobilized on a solid support ($BP_S$) and said competitor is attached to a first luminescent label selected from the group consisting of luminols and isoluminols ($C_L$); and
(iii) a second test reagent comprising an internal reference material corresponding to said substance, wherein said internal reference material is attached to a second luminescent label selected from the group consisting of acridinium esters and benzacridinium esters ($C_I$),
(b) reacting said test mixture to form a specific binding complex comprising either $BP_S$-substance, $BP_S$-$C_L$ or $BP_S$-$C_I$;
(c) separating said complex from unbound $C_L$ and $C_I$,
(d) activating said first luminescent label in the presence of an oxidation catalyst at a first pH process condition to emit a first measurable light emission wherein said first pH process condition does not activate said second luminescent label;
(e) measuring said first light emission;
(f) activating said second luminescent label at a second pH process condition to emit a second measurable light emission;
(g) measuring said second light emission; and
(h) correlating the first light emission to the presence or amount of said substance present in said test sample and correlating the second light emission to the presence or amount of said internal reference material,
wherein said first pH condition is a pH level lower than said second pH condition.

13. A method according to claim 12 wherein said first luminescent label is selected from the group consisting of N-(4-aminobutyl)-N-ethylisoluminol and 5-amino-2,3-dihydro-1,4-phthalazine dione and said second luminescent label is dimethyl acridinium ester.

14. A method according to claim 12 wherein said first pH condition is 7.4.

15. A method according to claim 12 wherein said second label is activated upon the sequential addition of a first solution comprising hydrogen peroxide and nitric acid followed by a second solution comprising sodium hydroxide.

16. A method according to claim 15 wherein said first label is activated with an activating agent comprising hydrogen peroxide in the presence of a microperoxidase catalyst and said first label is N-(4-aminobutyl)-N-ethylisoluminol.

17. A dual luminescent label specific binding assay for detecting a substance in a test sample and an internal reference material comprising the steps of:
(a) forming a test reaction mixture comprising:
(i) a test sample comprising a substance to be detected or quantitated;
(ii) a first test reagent comprising first and second binding partners which specifically bind to said substance, wherein said first binding partner is attached to a first luminescent label selected from the group consisting of luminols and isoluminols ($BP1_L$) and said second binding partner is immobilized on a solid support ($BP2_S$); and
(iii) a second test reagent comprising an internal reference material corresponding to said substance, wherein said internal reference material is attached to a second luminescent label selected from the group consisting of acridinium esters and benzacridinium esters ($C_L$);
(b) reacting said test mixture to form a specific binding complex comprising either $BP2_S$-substance-$BP1_L$ or $BP2_S$-$C_I$-$BP1_L$;
(c) separating said complex from unbound $BP1_L$ and unbound $C_I$;
(d) activating said first luminescent label in the presence of an oxidation catalyst at a first pH process condition to emit a first measurable light emission from said first luminescent label, wherein said first pH process condition does not activate said second luminescent label;
(e) measuring said first light emission;
(f) activating said second luminescent label at a second pH process condition to emit a second measurable light emission from said second luminescent label;
(g) measuring said second light emission; and
(h) correlating the first light emission to the presence or amount of said substance present in said test sample and correlating the second light emission to the presence or amount of said internal reference material,
wherein said first pH condition is a pH level lower than said second pH condition.

18. A method according to claim 17 wherein said assay is a hybridization assay said first luminescent label is selected from the group consisting of N-(4-aminobutyl)-N-ethylisoluminol and 5-amino-2,3-dihydro-1,4-phthalazine and said second luminescent label is dimethyl acridinium ester.

19. A method according to claim 17 wherein said first pH condition is 7.4.

20. A method according to claim 17 wherein said second label is activated upon the sequential addition of a first solution comprising hydrogen peroxide and nitric acid followed by a second solution comprising sodium hydroxide.

21. A method according to claim 20 wherein said first label is activated with an activating agent comprising hydrogen peroxide in the presence of a microperoxidase catalyst and said first label is N-(4-aminobutyl)-N-ethylisoluminol.

22. A dual luminescent label assay for detecting or measuring two substances in a sample comprising the sequential steps of:
(a) forming a test reaction mixture comprising:
(i) a test sample comprising a first substance and a second substance;

(ii) a first test reagent comprising a first binding partner (BP1) which specifically binds to said first substance wherein said first binding partner is immobilized on a solid support ($BP1_S$) and a second specific binding partner (BP2) which specifically binds to said first substance, wherein said second binding partner is attached to a first luminescent label selected from the group consisting of luminols and isoluminols ($BP2_L$); and (iii) a second test reagent comprising a third binding partner (BP3) which specifically binds to said second substance and a competitor which competes with said second substance for binding to said third binding partner, wherein said third binding partner is immobilized on a solid support ($BP3_S$) and said competitor is attached to a second luminescent label selected from the group consisting of acridinium esters and benzacridinium esters ($C_L$), (b) reacting said test mixture to form a first specific binding complex comprising $BP1_S$-first substance-$BP2_L$, and a second specific binding complex comprising either $BP3_S$-second substance or $BP3_S$-$C_L$;

(c) separating said first complex from unbound $BP2_L$ and separating said second complex from unbound $C_L$;

(d) activating said first luminescent label in the presence of an oxidation catalyst at a first pH process condition to emit a first measurable light emission from said first luminescent label, wherein said first pH process condition does not activate said second luminescent label;

(e) measuring said first light emission;

(f) activating said second luminescent label at a second pH process condition to emit a second measurable light emission;

(g) measuring said second light emission; and (h) correlating the first light emission to the presence or amount of said first substance and correlating the second light emission to the presence or amount of said second substance present in said test sample, wherein said first pH condition is a pH level lower than said second pH condition.

23. A method as recited in claim 22 wherein said first luminescent label is selected from the group consisting of N-(4-aminobutyl)-N-ethylisoluminol and 5-amino-2,3-dihydro-1,4-phthalazine dione and said second luminescent label is dimethyl acridinium ester.

24. A method according to claim 22 wherein said first pH condition is 7.4.

25. A method according to claim 22 wherein said second label is activated upon the sequential addition of a first solution comprising hydrogen peroxide and nitric acid followed by a second solution comprising sodium hydroxide and said first label is N-(4-aminobutyl)-N-ethylisoluminol.

26. A method according to claim 25 wherein said first label is activated with an activating agent comprising hydrogen peroxide in the presence of a microperoxidase catalyst.

27. A dual luminescent label specific binding assay for detecting or measuring a substance and an internal reference material comprising the sequential steps of:

(a) forming a test reaction mixture comprising:
(i) a test sample comprising a substance to be detected or quantitated;
(ii) a first test reagent comprising an internal reference material corresponding to said substance, wherein said internal reference material is attached to a first luminescent label selected from the group consisting of luminols and isoluminols ($C_I$); and (iii) a second test reagent comprising a specific binding partner which specifically binds to said substance and a competitor which competes with said substance, wherein said binding partner is immobilized on a solid support ($BP_S$) and said competitor is attached to a second luminescent label selected from the group consisting of acridinium esters and benzacridinium esters ($C_L$), (b) reacting said test mixture to form a first specific binding complex comprising $BP_S$-substance, $BP_S$-$C_L$ or $BP_S$-$C_I$;

(c) separating said complex from said unbound $C_L$ and unbound $C_I$;

(d) activating said first luminescent label in the presence of an oxidation catalyst at a first pH process condition to emit a first measurable light emission from said first luminescent label, wherein said first pH process condition does not activate said second luminescent label;

(e) measuring said first light emission;

(f) activating said second luminescent label at a second pH process condition to emit a second measurable light emission;

(g) measuring said second light emission; and (h) correlating the first light emission to the presence or amount of said internal reference material and correlating the second light emission to the presence or amount of said substance present in said test sample, wherein said first pH condition is a pH level lower than said second pH condition.

28. A method according to claim 27 wherein said first luminescent label is selected from the group consisting of N-(4-aminobutyl)-N-ethylisoluminol and 5-amino-2,3-dihydro-1,4-phthalazine dione and said second luminescent label is dimethyl acridinium ester.

29. A method according to claim 28 wherein said first pH condition is 7.4.

30. A method according to claim 27 wherein said second label is activated upon the sequential addition of a first solution comprising hydrogen peroxide and nitric acid followed by a second solution comprising sodium hydroxide and said first label is N-(4-aminobutyl)-N-ethylisoluminol.

31. A method according to claim 30 wherein said first label is activated with an activating agent comprising hydrogen peroxide in the presence of a microperoxidase catalyst.

32. A dual luminescent label specific binding assay for detecting or measuring a substance and an internal reference material comprising the sequential steps of:

(a) forming a test reaction mixture comprising:
(i) a test sample comprising a substance to be detected or quantitated;
(ii) a first test reagent comprising an internal reference material corresponding to said substance, wherein said internal reference material has attached thereto a first luminescent label selected from the group consisting of luminols and isoluminols ($C_L$); and
(iii) a second test reagent comprising first and second specific binding partners which specifically bind to said substance, wherein said first binding partner is immobilized on a solid support ($BP1_S$) and said second binding partner is attached to a second luminescent label selected from the group consisting of acridinium esters and benzacridinium esters ($BP2_L$), (b) reacting said test mixture to form a specific binding complex comprising either $BP1_S$-substance-$BP2_L$ or $BP1_S$-$C_I$-$B2P_L$;

(c) separating said complexes from unbound $C_I$ and $BP2_L$;

(d) activating said first luminescent label in the presence of an oxidation catalyst at a first pH process condition to emit a first measurable light emission from said first luminescent label, wherein said first pH process condition does not activate said second luminescent label;

(e) measuring said first light emission;

(f) activating said second luminescent label at a second pH process condition to emit a second measurable light emission;

(g) measuring said second light emission; and (h) correlating the first light emission to the presence or amount of said internal reference material and correlating the second light emission to the presence or amount of said substance present in said test sample, wherein said first pH condition is a pH level lower than said second pH condition.

33. A method according to claim 32 wherein said first pH condition is 7.4 and said first luminescent label is selected from the group consisting of N-(4-aminobutyl)-N-ethylisoluminol and 5-amino-2,3-dihydro-1,4-phthalazine and said second luminescent label is dimethyl acridinium ester.

34. A method according to claim 32 wherein said second label is activated upon the sequential addition of a first solution comprising hydrogen peroxide and nitric acid followed by a second solution comprising sodium hydroxide.

35. A method according to claim 34 wherein said first label is activated with an activating agent comprising hydrogen peroxide in the presence of a microperoxidase catalyst and said first label is N-(4-aminobutyl)-N-ethylisoluminol.

36. A dual luminescent label specific binding assay for detecting two substances in a sample comprising the sequential steps of:

(a) forming a test reaction mixture comprising:

(i) a test sample comprising a first substance and a second substance to be detected or quantitated;

(ii) a first test reagent comprising a first binding partner which specifically binds to said first substance and a competitor which competes with said first substance for binding to said first binding partner wherein said first binding partner is immobilized on a solid support ($BP1_S$), and wherein said competitor to said first substance is attached to a first luminescent label selected from the group consisting of luminols and isoluminols ($C_L$); and (iii) a second test reagent comprising a second binding partner (BP2) which specifically binds to said second substance, wherein said second binding partner is attached to a second luminescent label selected from the group consisting of acridinium esters and benzacridinium esters ($BP2_L$), and a third binding partner (BP3) which specifically binds to said second substance, wherein said third binding partner is immobilized on a solid support ($BP3_S$), (b) reacting said test mixture to form a first specific binding complex comprising $BP1_S$-first substance or $BP1_S$-$C_L$, and a second complex comprising $BP2_L$-second substance-$BP3_S$;

(c) separating said complexes from unbound $BP2_L$ and unbound $C_L$;

(d) activating said first luminescent label in the presence of an oxidation catalyst at a first pH process condition to emit a first measurable light emission from said first luminescent label, wherein said first pH process condition does not activate said second luminescent label;

(e) measuring said first light emission;

(f) activating said second luminescent label at a second pH process condition to emit a second measurable light emission from said second luminescent label;

(g) measuring said second light emission; and (h) correlating the first light emission to the presence or amount of said first substance and correlating the second light emission to the presence or amount of said second substance present in said test sample, wherein said first pH condition is a pH level lower than said second pH condition.

37. A method according to claim 36 wherein said second label is activated upon the sequential addition of a first solution comprising hydrogen peroxide and nitric acid followed by a second solution comprising sodium hydroxide and said first luminescent label is selected from the group consisting of N-(4-aminobutyl)-N-ethylisoluminol and 5-amino-2,3-dihydro-1,4-phthalazine and said second luminescent label is dimethyl acridinium ester.

38. A method according to claim 36 wherein said first label is activated with an activating agent comprising hydrogen peroxide in the presence of a microperoxidase catalyst and said first label is N-(4-aminobutyl)-N-ethylisoluminol.

* * * * *